US012691278B1

(12) United States Patent
Hunter

(10) Patent No.: US 12,691,278 B1
(45) Date of Patent: Jul. 28, 2026

(54) THERAPEUTIC VEST

(71) Applicant: Charles Hunter, Florence, SC (US)

(72) Inventor: Charles Hunter, Florence, SC (US)

( * ) Notice: Subject to any disclaimer, the term of this patent is extended or adjusted under 35 U.S.C. 154(b) by 435 days.

(21) Appl. No.: 18/411,994

(22) Filed: Jan. 12, 2024

Related U.S. Application Data

(63) Continuation-in-part of application No. 16/985,278, filed on Aug. 5, 2020, now abandoned.

(51) Int. Cl.
*A61N 1/04* (2006.01)
*A41D 1/04* (2006.01)
(Continued)

(52) U.S. Cl.
CPC ............. *A61N 1/0484* (2013.01); *A41D 1/04* (2013.01); *A61F 7/007* (2013.01); *A61H 23/02* (2013.01); *A41D 2400/322* (2013.01); *A61F 2007/0018* (2013.01); *A61F 2007/0036* (2013.01); *A61F 2007/0075* (2013.01); *A61F 2007/0078* (2013.01); *A61H 2201/02* (2013.01); *A61H 2201/10* (2013.01); *A61H 2201/1604* (2013.01);
(Continued)

(58) Field of Classification Search
CPC .................. A61H 1/00; A61H 2201/10; A61H 2201/165; A61H 23/00–06; A61H 2023/002–045; A61H 1/001–008; A61H 9/000092; A61H 2009/0014–0064; A41D 1/04; A41D 20/00; A41D 2400/322; A61F 7/007; A61F 2007/0002; A61F 2007/0036; A61F 2007/008; A61F 2007/0234; A61N 1/0456; A61N 1/0484; A61N 1/36021
See application file for complete search history.

(56) References Cited

U.S. PATENT DOCUMENTS 3,721,246 A * 3/1973 Landis ................. A61N 1/0492
607/115
4,926,879 A * 5/1990 Sevrain .................... G08B 6/00
340/407.1
(Continued)

FOREIGN PATENT DOCUMENTS

CN 109621150 A * 4/2019 ............ A61M 21/00
CN 219149014 U * 6/2023 ......... A61N 1/36014
(Continued)

*Primary Examiner* — Tu A Vo

(74) *Attorney, Agent, or Firm* — Gulf Coast Intellectual Property Group

(57) ABSTRACT

A therapy vest configured to provide three types of therapy to a wearer in order to provide relief from pain. The therapy vest includes a body that is configured to be worn on a human torso. The body includes an inner surface wherein the inner surface has disposed thereon a plurality of stimulation nodules. Each of the stimulation nodules are operable to provide vibration from a vibratory motor and further provide transcutaneous electrical nerve stimulation. The aforementioned can be provided simultaneously or separately. The body further includes a thermoelectric element disposed throughout wherein the thermoelectric element provides heating and cooling of the therapy vest. A head member is operably coupled to the vest and is configured to be surroundably mounted to the head of a wearer and provide the three types of therapy mentioned herein. A pair of glove members are further present to provide the therapy to the hands.

13 Claims, 2 Drawing Sheets

(51) Int. Cl.
*A61F 7/00* (2006.01)
*A61H 23/02* (2006.01)

(52) U.S. Cl.
CPC ................ *A61H 2201/1609* (2013.01); *A61H 2201/1619* (2013.01); *A61H 2201/1635* (2013.01); *A61H 2201/165* (2013.01)

(56) References Cited

U.S. PATENT DOCUMENTS

| | | | | |
|---|---|---|---|---|
| 5,018,521 A * | 5/1991 | Campbell | ................. | A61F 7/02 |
| | | | | 607/98 |
| 6,193,678 B1 * | 2/2001 | Brannon | ........... | A61H 23/0263 |
| | | | | 601/79 |
| 6,408,200 B1 * | 6/2002 | Takashina | ........... | A61B 5/6831 |
| | | | | 600/382 |
| 7,207,953 B1 * | 4/2007 | Goicaj | ................... | A61H 23/02 |
| | | | | 601/134 |
| 2002/0077688 A1 * | 6/2002 | Kirkland | ........... | A61N 1/36034 |
| | | | | 607/142 |
| 2004/0201521 A1 * | 10/2004 | Alvarez | ................. | G01S 19/25 |
| | | | | 342/357.62 |
| 2004/0260211 A1 * | 12/2004 | Maalouf | ................ | A61H 23/02 |
| | | | | 601/70 |
| 2007/0197941 A1 * | 8/2007 | Koen | ..................... | A61H 7/001 |
| | | | | 601/79 |
| 2009/0165183 A1 * | 7/2009 | Kerr | ..................... | A41D 13/005 |
| | | | | 2/2.5 |
| 2013/0204169 A1 * | 8/2013 | Poepperling | .......... | A61H 23/02 |
| | | | | 601/46 |
| 2013/0289455 A1 * | 10/2013 | Clapp | .................. | A61H 9/0007 |
| | | | | 601/149 |
| 2015/0305974 A1 * | 10/2015 | Ehrenreich | .......... | A61B 5/6833 |
| | | | | 601/46 |
| 2016/0120470 A1 * | 5/2016 | Bogdanovich | ....... | A61B 5/0002 |
| | | | | 340/870.07 |
| 2016/0242646 A1 * | 8/2016 | Obma | .................. | A61B 5/0024 |
| 2016/0317383 A1 * | 11/2016 | Stanfield | ............ | A61N 1/36031 |
| 2016/0346153 A1 * | 12/2016 | Hodges, IV | .......... | A61H 23/02 |
| 2018/0190094 A1 * | 7/2018 | Gill | ........................ | G08B 21/02 |
| 2019/0132948 A1 * | 5/2019 | Longinotti-Buitoni | ...................... | |
| | | | | A61B 5/0022 |
| 2020/0068708 A1 * | 2/2020 | Longinotti-Buitoni | ...................... | |
| | | | | A61B 5/0022 |
| 2020/0139119 A1 * | 5/2020 | Monteiro | .......... | A61N 1/36185 |
| 2020/0188224 A1 * | 6/2020 | Mountjoy | ............... | A61H 1/00 |
| 2020/0222276 A1 * | 7/2020 | Northen | ................... | A61H 1/00 |
| 2020/0282224 A1 * | 9/2020 | Lu | ........................ | A61N 1/0484 |
| 2020/0329788 A1 * | 10/2020 | Su | ...................... | A41D 13/0053 |
| 2020/0390172 A1 * | 12/2020 | Kaib | .................... | A41D 31/102 |
| 2020/0405168 A1 * | 12/2020 | Gabrin | .................. | A61B 5/361 |
| 2021/0059332 A1 * | 3/2021 | Fernandez | ......... | A61H 23/0263 |
| 2021/0178172 A1 * | 6/2021 | Kim | ...................... | A61N 1/046 |
| 2021/0401075 A1 * | 12/2021 | Gruentzig | ........... | A41D 13/018 |

FOREIGN PATENT DOCUMENTS

| | | | | | |
|---|---|---|---|---|---|
| KR | 20210114615 A | * | 9/2021 | ........ | A41D 13/0053 |
| KR | 20230049185 A | * | 4/2023 | ........ | A61H 23/0254 |
| WO | WO-2017081352 A1 | * | 5/2017 | ............ | A61H 23/02 |

* cited by examiner

THERAPEUTIC VEST

CROSS REFERENCE TO RELATED APPLICATIONS

This application is a continuation-in-part of U.S. patent application Ser. No. 16/985,278 filed, Aug. 5, 2020, entitled, Therapeutic Vest, in the name of Charles Hunter, which is hereby incorporated for reference.

FIELD OF THE INVENTION

The present invention relates generally to therapeutic devices, more specifically but not by way of limitation, a therapeutic vest wherein the vest is configured to deliver temperature therapy to the torso, head and hands of a wearer and further provide massage implementation to the afore-mentioned areas of the human body.

BACKGROUND

Massage therapy has been practiced for hundreds of years and is well known to have health benefits as well as provide relief for muscle pain. Some of the physical benefits of massage and myotherapy include but are not limited to reduced muscle tension, increased circulation, reduced stress and improved recovery of soft tissue injuries. It is common for various conditions to have suggested by a health care practitioner to receive massage therapy on a routine basis. Conventionally there are generally two meth-ods to deliver massage therapy wherein one is utilizing a massage device and the other is to procure the services of a massage therapist. The latter is quite costly and can be inconvenient of an individual is required to utilize massage therapy on a fairly routine basis. The conventional devices available includes motorized rods and other small structures that employ vibratory motors but these devices are only focused on one small area of the body and can not deliver massage therapy simultaneously to multiple sections of the body.

Temperature therapy is also commonly utilized to treat various muscular ailments. Heating pads are commonly utilized to treat sore muscles such as but not limited to sore back muscles. Heat improves the circulation and facilitates an improved recovery time for damaged muscle tissue. In addition to heat, it is known in the art that cool temperatures can provide therapeutic benefits such as but not limited to swelling reduction. Heating and cooling are typically deliv-ered via conventional heating pads and ice packs which are confined to small sizes and placed on specific locations of the body and are not configured to provide temperature therapy to larger portions of the body.

Accordingly, there is a need for a therapeutic vest that is configured to be worn by a user wherein the vest of the present invention provides massage and temperature therapy to the entire torso, sections thereof or extremities of the wearer of the vest of the present invention.

SUMMARY OF THE INVENTION

It is the object of the present invention to provide a therapeutic vest configured to be worn by a user and provide massage and temperature therapy thereto wherein the pres-ent invention includes a vest body that is configured to surroundably mount the torso of a user.

Another object of the present invention is to provide a therapeutic device that is operable to provide massage and/or temperature therapy to a user wherein the vest body of the present invention includes an inner surface having a plurality of vibratory motors.

A further object of the present invention is to provide a therapeutic vest configured to be worn by a user and provide massage and temperature therapy thereto that further includes a head unit wherein the head unit is configured to be donned on a head of a user and wherein the head unit is operably coupled to the vest body.

Still another object of the present invention is to provide a therapeutic device that is operable to provide massage and/or temperature therapy to a user wherein the vest body further includes a belt portion having additional massaging vibratory motors disposed therein.

An additional object of the present invention is to provide a therapeutic vest configured to be worn by a user and provide massage and temperature therapy thereto wherein the present invention further includes glove members wherein the glove members of the present invention include temperature controllers and vibratory motors.

Yet a further object of the present invention is to provide a therapeutic device that is operable to provide massage and/or temperature therapy to a user wherein the vest body further includes pad members proximate the rear area thereof.

Another object of the present invention is to provide a therapeutic vest configured to be worn by a user and provide massage and temperature therapy thereto wherein the pres-ent invention includes a controller configured to provide operational control thereof.

Still an additional object of the present invention is to provide a therapeutic device that is operable to provide massage and/or temperature therapy to a user is to provide a software application that is configured to operably control the present invention utilizing a smart phone or similar computing device.

A further object of the present invention is to provide a therapeutic vest configured to be worn by a user and provide massage and temperature therapy thereto that employs Pel-tier style elements with a power supply to generate heating and cooling of portions of the present invention.

To the accomplishment of the above and related objects the present invention may be embodied in the form illus-trated in the accompanying drawings. Attention is called to the fact that the drawings are illustrative only. Variations are contemplated as being a part of the present invention, limited only by the scope of the claims.

BRIEF DESCRIPTION OF THE DRAWINGS

A more complete understanding of the present invention may be had by reference to the following Detailed Descrip-tion and appended claims when taken in conjunction with the accompanying Drawings wherein:

DETAILED DESCRIPTION

Figures 1, 2:
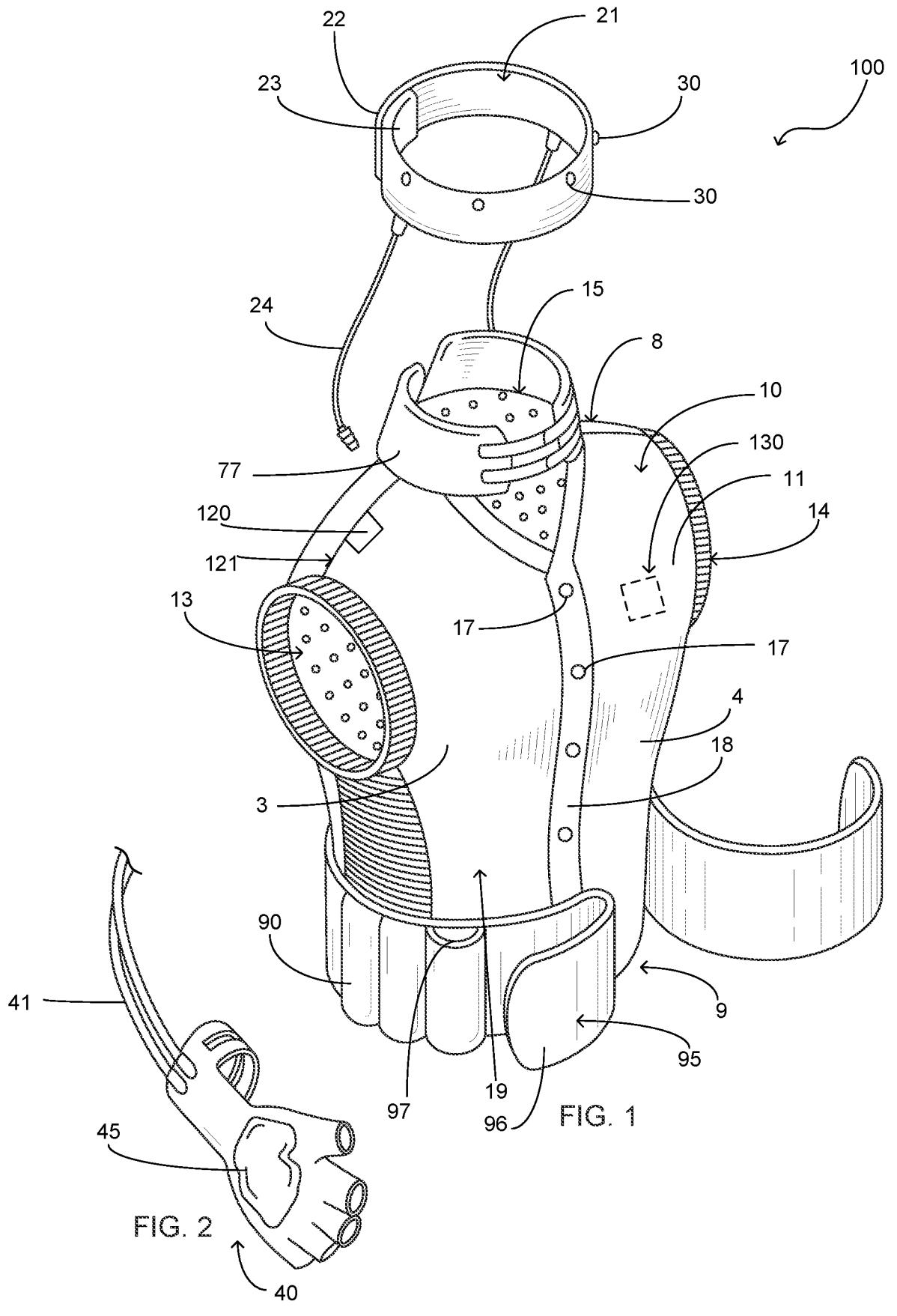
FIG. 1 is a perspective view of an embodiment of the present invention.
FIG. 2 is a detailed view of the glove member of the present invention.

Referring now to the drawings submitted herewith, wherein various elements depicted therein are not necessarily drawn to scale and wherein through the views and figures like elements are referenced with identical reference numerals, there is illustrated a therapy vest 100 constructed according to the principles of the present invention.

An embodiment of the present invention is discussed herein with reference to the figures submitted herewith. Those skilled in the art will understand that the detailed description herein with respect to these figures is for explanatory purposes and that it is contemplated within the scope of the present invention that alternative embodiments are plausible. By way of example but not by way of limitation, those having skill in the art in light of the present teachings of the present invention will recognize a plurality of alternate and suitable approaches dependent upon the needs of the particular application to implement the functionality of any given detail described herein, beyond that of the particular implementation choices in the embodiment described herein. Various modifications and embodiments are within the scope of the present invention.

It is to be further understood that the present invention is not limited to the particular methodology, materials, uses and applications described herein, as these may vary. Furthermore, it is also to be understood that the terminology used herein is used for the purpose of describing particular embodiments only, and is not intended to limit the scope of the present invention. It must be noted that as used herein and in the claims, the singular forms "a", "an" and "the" include the plural reference unless the context clearly dictates otherwise. Thus, for example, a reference to "an element" is a reference to one or more elements and includes equivalents thereof known to those skilled in the art. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

References to "one embodiment", "an embodiment", "exemplary embodiments", and the like may indicate that the embodiment(s) of the invention so described may include a particular feature, structure or characteristic, but not every embodiment necessarily includes the particular feature, structure or characteristic.

Referring in particular to the Figures submitted as a part hereof, the therapy vest 100 includes a vest member 10. The vest member 10 is configured to be worn by a user on their torso. The vest member 10 is manufactured from a durable comfortable material such as but not limited to nylon. The vest member 10 includes a body 11 that is configured with two arm apertures 13,14 and a neck aperture 15 wherein the aforementioned are configured to allow arms and neck to be journaled therethrough respectively. The vest member 10 includes securing members 17 wherein the securing members are operable to releasably secure opposing halves 3,4 of the front of the body 11 of the vest member 10. The securing members 17 extend longitudinally along the front 19 of the body 10 intermediate the top end 8 and bottom end 9. It is contemplated within the scope of the present invention that the securing members 17 could be elements such as but not limited to buttons or snaps that are configured to releasably secure the opposing halves 3,4 of the front 19 along seam 18. While a particular configuration for the seam 18 and securing members 17 are illustrated herein, it is contemplated within the scope of the present invention that the body 10 could be provided in alternate configurations in order to facilitate the donning and removal thereof.

Operably coupled to the vest member 10 is the head member 20. The head member 20 is configured to surroundably mount the head of the wearer of the therapy vest 100. The head member 20 includes a band 21 wherein the band 21 includes a first end 22 and second end 23 that are configured to be releasably secured. The first end 22 and second end 23 are configured to be releasably secured utilzing materials such as but not limited to hook and loop so as to adjustable fit various sizes of human heads. The head member 20 is operably coupled to the vest member 10 via cables 24. Cables 24 supply the necessary electrical current to operate the stimulatory members 30. The stimulatory members 30 are configured to provide both vibratory stimulation and electrical stimulation to the head of the user of the therapy vest 100. The stimulatory members 30 include both a vibratory motor and a transcutaneous electrical nerve stimulation (TENS) operable to provide an electrical current to the area of the body of the user adjacent thereto. The vibratory motor is a conventional direct current operated off balance motor configured to emit vibrations, which are transmitted to the head of the wearer. Furthermore, the stimulatory members 30 are configured to provide an electrical voltage to the head of the user. The electrical voltage floods the nervous system so as to inhibit the transmission of pain signals and further stimulates the production of endorphins. It should be understood within the scope of the present invention that the head member 20 could have various quantities of stimulatory members 30 secured thereon. It should be understood within the scope of the present invention that the therapy vest 100 could be utilized with or without the head member 20.

The therapy vest 100 further includes glove member 40. Glove member 40 is configured to surroundably mount the hand of a user. The glove member 40 is operably coupled to the vest member 10 via cables 41 which are configured to transmit the necessary voltage to operate the glove member 40. The glove member 40 has integrally formed therewith a stimulation section 45. The stimulation section 45 is configured to provide both TENS and vibration to the hand disposed therein. The stimulation section 45 includes at least one vibratory motor and at least one TENS nodule that are configured to provide vibration and electrical stimulation either separately or simultaneously. While the stimulation section 45 is illustrated in a particular location on the glove member 40 herein, it should be understood within the scope of the present invention that the glove member 40 could have more than one stimulation section 45 and further the stimulation section 45 could be placed in alternate locations. While only on glove member 40 is illustrated herein, it should be understood within the scope of the present invention that the therapy vest 100 has two glove members 40 one for each hand of the user. It should be further understood within the scope of the present invention that the therapy vest 100 could be operated with or without the glove members 40.

The vest member 10 includes an inner surface 50. The inner surface 50 is adjacent the torso of a user ensuing the user donning the therapy vest 100. The inner surface 50 has disposed thereon a plurality of stimulation nodules 60. The stimulation nodules 60 are distributed substantially across the inner surface 50 of the vest member 10. The stimulation nodules 60 are configured to provide both TENS and vibration to the torso of the user. It should be understood within the scope of the present invention that the stimulation nodules 60 include at least one vibratory motor and at least one TENS unit. While the inner surface 50 is illustrated in the preferred embodiment herein having the stimulation nodules 60 disposed substantially thereacross, it should be understood within the scope of the present invention that the inner surface 50 could have the stimulation nodules 60 concentrated in a particular portion thereof such as but not limited to the lower back area. Furthermore, it should be understood within the scope of the present invention that the stimulation nodules 60 could be separated into zones wherein a controller (not particularly illustrated herein) is operable to activate either all or only one or more of the zones.

Figures 3, 4:
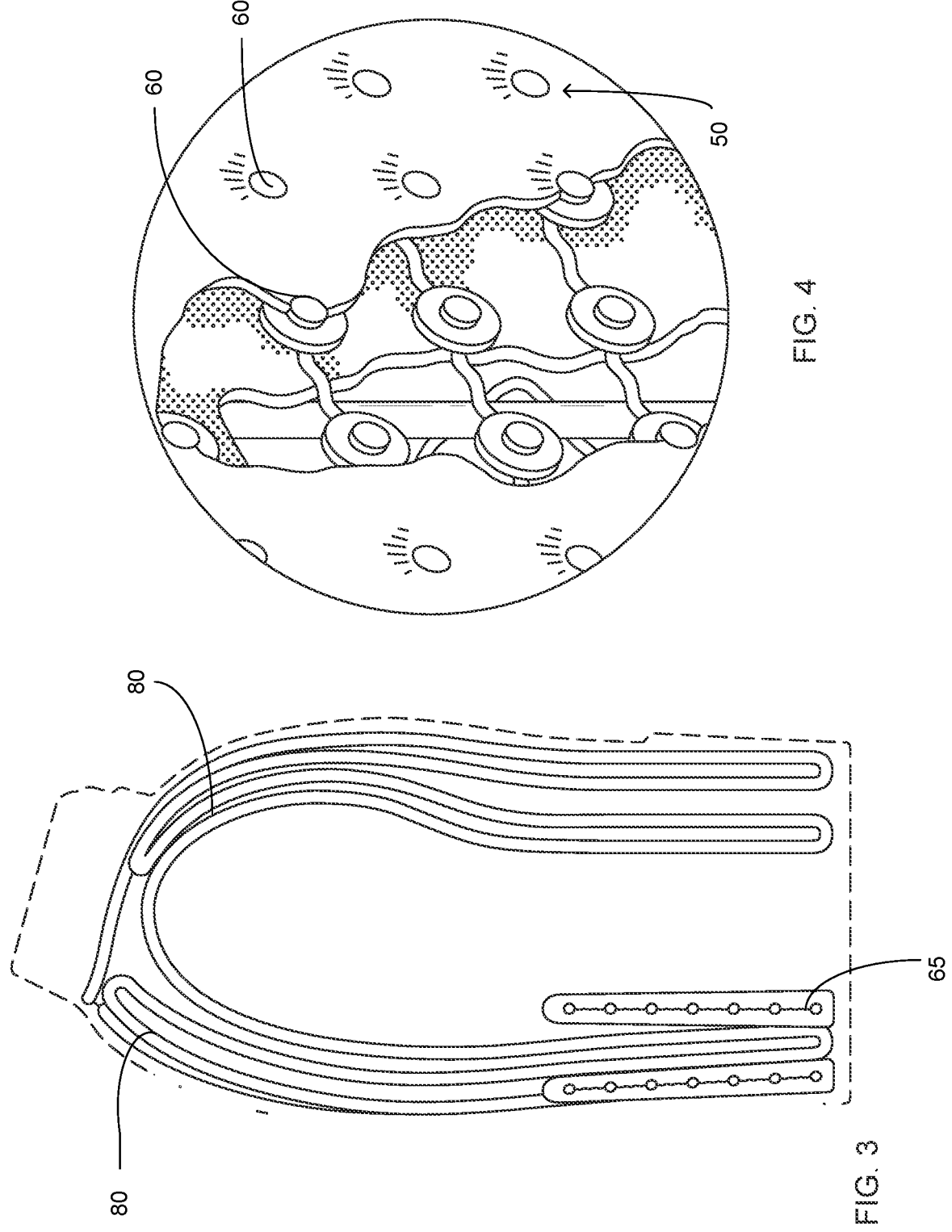
FIG. 3 is a cross sectional diagrammatic view of the present invention.
FIG. 4 is a detailed view of the interior surface of the vest member of the present invention.

Referring in particular to FIG. 3, the body 10 further includes pad member 65. Pad member 65 is configured to be proximate the lower back of a user ensuing a user donning the therapy vest 100. The pad member 65 is operable to provide increased comfort when sitting or just overall during use of the therapy vest 100. The pad member 65 is manufactured from a material such as but not limited to silicone gel. Furthermore, the pad member 65 can include the stimulation nodules 60 that are previously described herein. It should be understood within the scope of the present invention that the pad member 65 could be formed in various shapes, sizes and thickness in order to achieve the desired objective herein.

The therapy vest 100 further includes temperature members 80. The temperature members 80 are operable to provide either a heating or cooling of the torso of the wearer of the therapy vest 100. The temperature members 80 are manufactured from a pliable metal and are operably coupled to the power supply 90 of the present invention. The power supply 90 is configured to supply a direct current voltage to the temperature members in order to provide thermoelectric heating or cooling. Those skilled in the art will understand that the temperature members 80 utilize the Peltier effect to achieve the desired objective. The temperature members 80 are substantially disposed across the vest member 10 so as to provide entire heating or cooling thereof and as such transfer to the torso of the user. While in the preferred embodiment of the present invention the temperature members 80 are substantially disposed across the vest member 10, it should be understood within the scope of the present invention that the temperature members 80 could be disposed on only a portion of the vest member 10.

Operably secured to the vest member 10 is belt unit 95. Belt unit 95 is configured to releasably secure the vest member 10 proximate the waist of a user. Ends 96,97 are configured to be releasably secured utilizing suitable techniques such as but not limited to hook and loop material. The belt unit 95 has integrally formed therewith a controller pocket 97 and power supply 90. The power supply 90 provides the necessary direct current voltage to provide operation of the therapy vest 100. In a preferred embodiment of the therapy vest 100 the power supply 90 is a lithium ion battery. The controller pocket 97 is configured to receive an retain a controller (not illustrated herein) that is configured to control operation of the therapy vest 100. It is contemplated within the scope of the present invention that the controller could be either a directly coupled handheld unit or be a smart phone configured with a software application wherein both are configured to provide full operational control of the therapy vest 100.

The neck brace member 77 is integrally formed with the body 11 and is configured to circumferentially mount the neck of the user of the therapy vest. The neck brace member 77 is configured to provide the temperature control, vibration and TENS as described herein for alternate portions of the therapy vest 10. The neck brace member 77 is additionally manufactured from a stiffer more support material in order to provide support for a user that may have a neck injury.

The therapy vest 100 further includes a geolocation module 120. The geolocation module 100 is operable to provide transmission of the geolocation of a user of the therapy vest 100 to a third party. It should be understood within the scope of the present invention that the therapy vest 100 could have civilian and military applications and as such the third party could be alternate entities. The geolocation module 120 includes the necessary electronics to receive, store, transmit and manipulate data and is programmed to continuously monitor the geolocation of a user during use of the therapy vest 100. The geolocation module 120 is placed proximate a shoulder area 121 of the therapy vest 100 in order to maintain communicable coupling with geo location satellites in order to receive signals therefrom and maintain communication therewith. While the shoulder area 121 is the preferred embodiment, it is contemplated within the scope of the present invention that the geolocation module 120 could be placed in alternate locations on the therapy vest 100.

The therapy vest 100 additionally includes a vitals monitoring unit 130. The vitals monitoring unit 130 is embedded within the therapy vest 100 and includes the necessary electronics to receive, store, transmit and manipulate data. The vitals monitoring unit 130 provides capture of vital signs such as but not limited to the respiration rate, body temperature and heart rate of the user. The vitals monitoring unit 130 further includes a transmitter that transmits the aforementioned data to at least one third party in a remote location. It is intended within the scope of the present invention that the therapy vest 100 is employed for various applications wherein the user of the therapy vest 100 is monitored by a third party during use thereof. The vitals monitoring unit 130 provides continuous transmission of the vitals of the user wherein in the event of an abnormality thereof the third party can execute a strategy to request assistance for the wearer of the therapy vest 100. While in the preferred embodiment of the present invention the vitals monitoring unit 130 monitors the heart rate, respiration rate and body temperature, it is contemplated within the scope of the present invention that the vitals monitoring unit 130 could provide monitoring of alternate body vitals such as but not limited to blood pressure.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical changes may be made without departing from the spirit or scope of the invention. The description may omit certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A therapy vest configured to be worn by a user on a torso so as to provide pain relief wherein the therapy vest comprises:

a vest member, said vest member having a body, said body being configured to be releasably secured to the torso of the user, said body having an upper end and a lower end, said body having opposing arm apertures and a neck aperture, said vest member having a front portion wherein the front portion includes opposing halves releasably secured, said body having an inner surface, said inner surface of said body is configured to be adjacent to the torso of the user ensuing the user donning the therapy vest, wherein the inner surface has a plurality of stimulation nodules, said stimulation nodules being disposed substantially across the inner surface of said body of said vest member, said stimulation nodules configured to provide vibrations and electrical nerve stimulation;

a temperature member, said temperature member being disposed within the body of the vest member, said temperature member configured to alter a temperature of the body of the vest member to a temperature that is different than a temperature of an environmental surrounding that surrounds the vest member;

a pair of glove members, said pair of glove members being operably coupled to said vest member, said pair of glove members having at least one stimulation A section, said stimulation section configured to provide vibrations and electrical nerve stimulation to hands of the user;

a geolocation module, said geolocation module having electronics operable to receive, store, transmit and manipulate data related to the geolocation module, said geolocation module being mounted to said vest member proximate a shoulder area thereof, said geolocation module operable to ascertain a geographic location of the therapy vest and transmit the geographic location to a third party;

a vitals monitoring unit, said vitals monitoring unit being embedded within said vest member, said vitals monitoring unit having electronics configured to receive, store, transmit and manipulate data related to the vitals monitoring units, said vitals monitoring unit operable to monitor a heart rate, a respiration rate and a body temperature of a wearer of the therapy vest and transmit to the third party; and a power supply, said power supply configured to provide the necessary electrical power for the therapy vest.

2. The therapy vest as recited in claim 1, and further including a belt unit, said belt unit being operably secured to said body of said vest member proximate said lower end of said body, said belt unit member having a first end and a second end configured to be releasably secured, said belt unit configured to house said power supply and secure the vest member proximate a waist area of the user.

3. The therapy vest as recited in claim 2, and further including a neck brace member, said neck brace member configured to be surroundably mounted around a neck of the user, said neck brace member configured to provide support for the neck of the user.

4. The therapy vest as recited in claim 3, and further including a head member, said head member being operably coupled to the vest member, said head member having a first end and a second end configured to be releasably secured, said head member configured to circumferentially mount a head of the user, said head member having a plurality of stimulatory members, said stimulatory members configured to provide vibrations and electrical nerve stimulation to a head of the user.

5. The therapy vest as recited in claim 4, and further including a pad member, said pad member being disposed adjacent the inner surface of said body of said vest member, said pad member is configured to be adjacent to a lower back region of the torso of the user, said pad member being manufactured from silicone gel.

6. The therapy vest as recited in claim 5, wherein the temperature member is configured to heat or cool the body of the vest member.

7. The therapy vest as recited in claim 6, wherein the power supply is a lithium ion battery.

8. A therapy vest configured provide three types of stimulus therapy to a user so as to provide pain relief wherein the therapy vest comprises:

a vest member, said vest member having a body, said body being configured to be releasably secured to the torso of the user, said body having an upper end and a lower end, said body having opposing arm apertures and a neck aperture, said vest member having a front portion wherein the front portion includes opposing halves releasably secured, said opposing halves being bordered by a seam, said seam having securing members thereon wherein said securing members are operably to releasably secure said opposing halves, said body having an inner surface, said inner surface of said body is configured to be adjacent to the torso of the user ensuing the user donning the therapy vest, wherein the inner surface has a plurality of stimulation nodules, said stimulation nodules being disposed substantially across the inner surface of said body of said vest member, said stimulation nodules configured to provide vibrations and electrical nerve stimulation;

a temperature member, said temperature member being disposed within the body of the vest member, said temperature member configured to alter a temperature of the body of the vest member to a temperature that is different than a temperature of an environmental surrounding that surrounds the vest member;

a pair of glove members, said pair of glove members being operably coupled to said vest member, said pair of glove members having at least one stimulation section, said stimulation section configured to provide vibrations and electrical nerve stimulation to hands of the user;

a head member, said head member being operably coupled to the vest member, said head member having a first end and a second end configured to be releasably secured, said head member configured to circumferentially mount a head of the user, said head member having a plurality of stimulatory members, said stimulatory members configured to provide vibrations and electrical nerve stimulation to a head of the user;

a geolocation module, said geolocation module having electronics operable to receive, store, transmit and manipulate data related to the geolocation module, said geolocation module being mounted to said vest member proximate a shoulder area thereof, said geolocation module operable to ascertain the geographic location of the therapy vest and transmit a geographic location to a third party;

a vitals monitoring unit, said vitals monitoring unit being embedded within said vest member, said vitals monitoring unit having electronics configured to receive, store, transmit and manipulate data related to the vitals monitoring unit, said vitals monitoring unit operable to monitor a heart rate, a respiration rate and a body temperature of a wearer of the therapy vest and transmit to the third party; and a power supply, said power supply configured to provide the necessary electrical power for the therapy vest.

9. The therapy vest as recited in claim 8, and further including a belt unit, said belt unit being operably secured to said body of said vest member proximate said lower end of said body, said belt unit having a first end and a second end configured to be releasably secured, said belt unit configured to house said power supply and secure the vest member proximate a waist area of the user, said belt unit further having a controller pocket.

10. The therapy vest as recited in claim 9, wherein the temperature member is configured to heat or cool the body of the vest member.

11. The therapy vest as recited in claim 10, and further including a pad member, said pad member being disposed adjacent the inner surface of said body of said vest member, said pad member is configured to be adjacent to a lower back region of the torso of the user, said pad member being manufactured from silicone gel, said pad member further having said stimulation nodules thereon.

12. The therapy vest as recited in claim 11, wherein the power supply is a lithium ion battery.

13. The therapy vest as recited in claim 12, wherein the plurality of stimulation nodules are separated into zones wherein each zone is independently operable.

\*　\*　\*　\*　\*